United States Patent [19]
Niemann

[11] 3,939,258
[45] Feb. 17, 1976

[54] PROCESS FOR THE MANUFACTURE OF HUMAN TRANSFERRIN LABELLED WITH INDIUM 113M

[75] Inventor: Elfriede Niemann, Frankfurt am Main, Germany

[73] Assignee: Hoechst Aktiengesellschaft, Frankfurt am Main, Germany

[22] Filed: Aug. 9, 1973

[21] Appl. No.: 386,862

[30] Foreign Application Priority Data
Aug. 12, 1972  Germany............................ 2239791

[52] U.S. Cl................................ 424/1; 252/301.1 R
[51] Int. Cl.²........................................ A61K 43/00
[58] Field of Search................... 252/301.1 R; 424/1

[56] References Cited
OTHER PUBLICATIONS
"Red Cell and Plasma Protein Labeling with $^{113m}$In," International Journal of Applied Radiation and Isotopes, 1971, Vol. 22, No. 8, pp. 498–501.
Chemical Abstracts, Vol. 75, No. 19, Nov. 8, 1971, p. 78, Item No. 116531b.
Chemical Abstracts, Vol. 72, No. 15, Apr. 13, 1970, p. 85, Item No. 75562e.

Primary Examiner—Benjamin R. Padgett
Assistant Examiner—Christine M. Nucker
Attorney, Agent, or Firm—Curtis, Morris & Safford

[57] ABSTRACT

A process for the manufacture of human transferrin labelled with indium 113 $m$ is provided, wherein an acid eluate of an indium 113 m generator having an activity concentration of 0.1 to 50 m Curie per ml is added dropwise to an aqueous solution containing 3 to 10 mg of sodium bicarbonate per 5 to 100 mg of human transferrin per ml. The solution may also contain hydrochloric acid or sodium chloride and a bacteriostatic agent.

2 Claims, No Drawings

PROCESS FOR THE MANUFACTURE OF HUMAN TRANSFERRIN LABELLED WITH INDIUM 113M

The present invention relates to a process for the manufacture of human transferrin which is labelled with indium 113m.

The radioactive nuclide indium 113 m is used for diagnosis in nuclear medicine, for example for radiographic visualization of tumors. Indium 113 m may be obtained free from carrier substances, it has a favorable physical half life of 1.7 hours and a pure gamma ray emission of 373 KeV.

It is known that, after intravenous injection of indium 113 m chloride, part of indium 113 m is linked to transferrin in the human and animal organisms and is thus carried in the blood circulation (Literature references 1, 2, 3, 4 on page 4/5).

Transferrin is a beta globulin of the serum which usually brings about the transport of iron ions in the blood circulation. Labelling human transferrin with the short-life nuclide indium 113 m makes available a substance which, like the iron-charged transferrin, circulates in the blood vessels of man and hence serves for measuring the circulation and for visualizing the placenta.

It is known to label transferrin in the blood plasma with indium 113 m. This method is, however, disadvantageous since blood samples have first to be taken from the patient and plasma has to be obtained therefrom; further the reaction of the indium 113 m solution in hydrochloric acid with transferrin in the plasma might damage some proteins of the plasma, and still further the indium 113 m does not react quantitatively with transferrin in the plasma so that unreacted indium 113 m has to be eliminated from the plasma, for example by means of ion exchange resins (references 3, 4, 5).

It is also known to incubate a 5 % transferrin solution in veronal acetate buffer solution of pH 8.6 with an aliquot amount of a 0.05 N indium 113 m solution in hydrochloric acid; for this purpose, 20 ml of a 0.05 N eluate of an indium 113 m generator in hydrochloric acid are evaporated to dryness and the residue is taken up in 0.5 ml of a 0.05 N hydrochloric acid (reference 6). This method, however, is also disadvantageous since evaporation of the indium solution means high losses in activity due to the short half life of this nuclide and the veronal buffer solution is neither physiologically favorable nor isotonic. According to that method, the yield of labelled substance is not quantitative either.

The present invention relates to a process for the manufacture of human transferrin labelled with indium 113 m, which comprises adding dropwise an acid eluate of an indium 113 m generator having an activity concentration of from 0.1 to 50 milli Curie per ml to an aqueous solution containing, per 5 to 100 mg of human transferrin/ml, 3 to 10 mg of sodium bicarbonate and having a pH-value of from 7.5 to 8.5.

The solution of indium 113 m in hydrochloric acid may, for example, be obtained according to the method disclosed in U.S. Pat. No. 3,450,597, especially in Example 1.

It is advantageous to use an eluate containing 0.2 to 0.01 N hydrochloric acid.

It is suitable to isotonize the transferrin solution labelled with indium 113 m for injection purposes by adding sodium chloride, preferably in such an amount that after addition of the eluate in hydrochloric acid the resulting solution is isotonic.

Moreover, a suitable bacteriostatic agent, for example a mixture of the methyl and propyl esters of parahydroxy benzoic acid, may be added.

The pH-value of the transferrin solution is changed to 6 – 7.5 by adding the indium containing solution. The yield of labelled transferrin amounts to 100 per cent. A purification of the solution from unreacted indium is therfore not required. When sterile conditions are observed, the isotonic solution can directly be used for injection.

The administeration of transferrin labelled with indium 113 m to dogs and rats shows that the biological half life of this albumin in dogs exceeds 7 hours, thus corresponding approximately to that of albumin iodine 125. This observation and the repartition of indium 113 m found in the organs of test animals allow to conclude that the transferrin labelled with indium 113 m and prepared according to the process of the invention is suitable for a circulation control, radiocardiography and placenta scintigraphy.

References to literature:
1. J. E. Huddlestun, F. S. Mishkin, J. E. Carter, P. D. Dubois and J. C. Reese. Radiology 92 (1969), page 587
2. R. D. Neihoff, W. R. Hendee and D. W. Brown. Journal Nuclear Medicine 11 (1970), p. 15
3. H. S. Stern, D. A. Goodwin, U. Scheffel, H. N. Wagner and H. H. Kramer. Nucleonics 25 (1967), page 62.
4. F. Hosain, P. A. Mc Intyre, K. Poulose, H. S. Stern and H. N. Wagner. Clinical Chemistry A. 24 (1969), p. 69
5. S. E. Graber, P. J. Hurley, R.M. Heyssel and P.A. McIntyre Journal Experimental Biology and Medicine 133 (1970), p. 1093
6. Hundeshagen, H., Dopslaff, H. Meyer, D. Jahrestagung der Gesellschaft fur Nuklearmedizin Weisbaden 1068, K. Schattauer Verlag, Stuttgart.

The following Example illustrate the invention.

EXAMPLE:

An indium 113 m generator was eluted according to the method disclosed in U.S. Pat. No. 3,450,597, Example 1, at room temperature with 10 ml of a sterile 0.05 N hydrochloric acid. Especially useful were indium 113 m generators which have a tin 113 activity of 5 to 100 milli Curie so that the activity concentration of the eluate was 0.5 to 10 milli Curie per ml.

1 Milliliter of the eluate obtained was slowly added dropwise while constantly shaking to 1 ml of a sterile human transferrin solution having a concentration of 20 mg per ml and containing 6 mg of sodium bicarbonate, 13 mg of sodium chloride, 1.8 mg of PHB methyl ester and 0.2 mg of PHB propyl ester. The pH of this solution was 8.2 before the eluate had been added. After addition of the eluate the pH of the transferrin solution labelled with indium 113 m thus obtained was 6.2 to 6.5.

The yield of labelled substance could be determined with the aid of paper electrophoresis in veronal buffer at pH 8.6 over a period of 2 hours; it was 100 per cent. The transferrin labelled with indium 113 m was colored with amino black 10 B; radio activity was measured by radio paper chromatography.

Under sterile conditions 2 ml of a human transferrin solution labelled with indium 113 m and ready for injection were thus obtained.

I claim:

1. A method for making human transferrin labelled with indium 113m, which comprises adding an eluate of an indium 113m generator dropwise to an aqueous human transferrin solution in a volume ratio of 1:1, said eluate having an activity concentration of 0.9 to 50 milli Curie per ml and containing 0.2 to 0.01 N hydrochloric acid and said aqueous transferrin solution containing 3 to 10 mg of sodium bicarbonate per 5 to 100 mg of human transferrin per ml.

2. A method as in claim 1 wherein said transferrin solution additionally contains sodium chloride and, as a bacteriostatic agent, a mixture of the methyl and propyl esters of parabenzoic acid.

* * * * *